United States Patent
Cronin et al.

(10) Patent No.: US 8,786,839 B2
(45) Date of Patent: Jul. 22, 2014

(54) OBJECT AUTHENTICATION

(71) Applicant: Authentix, Inc., Addison, TX (US)

(72) Inventors: Paul J. Cronin, Allen, TX (US); Chester Wildey, Euless, TX (US); Alan K. Hunt, Dallas, TX (US)

(73) Assignee: Authentix, Inc., Addison, TX (US)

( * ) Notice: Subject to any disclaimer, the term of this patent is extended or adjusted under 35 U.S.C. 154(b) by 0 days.

(21) Appl. No.: 14/024,074

(22) Filed: Sep. 11, 2013

(65) Prior Publication Data

US 2014/0009752 A1    Jan. 9, 2014

Related U.S. Application Data

(63) Continuation of application No. 13/487,442, filed on Jun. 4, 2012, now Pat. No. 8,547,537, which is a continuation of application No. 12/904,908, filed on Oct. 14, 2010, now Pat. No. 8,194,237.

(60) Provisional application No. 61/251,915, filed on Oct. 15, 2009.

(51) Int. Cl.
G06K 9/74 (2006.01)
G06K 9/00 (2006.01)
A61B 5/117 (2006.01)

(52) U.S. Cl.
CPC ............... *G06K 9/00046* (2013.01); *A61B 5/1172* (2013.01)
USPC ........................................... 356/71

(58) Field of Classification Search
CPC ............................ G06K 9/00046
USPC ........................................... 356/71
See application file for complete search history.

(56) References Cited

U.S. PATENT DOCUMENTS

| 4,525,630 A | 6/1985 | Chapman |
| 4,670,779 A | 6/1987 | Nagano |
| 4,922,109 A | 5/1990 | Bercovitz et al. |
| 5,304,813 A | 4/1994 | De Man |

(Continued)

FOREIGN PATENT DOCUMENTS

| CA | 2682467 A1 | 10/2008 |
| DE | 102004035494 A1 | 2/2006 |

(Continued)

OTHER PUBLICATIONS

Filing receipt and specification for provisional patent application entitled "Document Authentication Sensor," by Paul J. Cronin, et al., filed Oct. 15, 2009 as U.S. Appl. No. 61/251,915.

(Continued)

*Primary Examiner* — Michael P Stafira
(74) *Attorney, Agent, or Firm* — Conley Rose, P.C.; Rodney B. Carroll

(57) ABSTRACT

A device detects multi-spectral imaging by using scan elements. The device may include an illumination module and a detection module to detect light scattered from an object illuminated by the illumination module. The device may also include an array of light sources to produce light at a plurality of different wavelengths, and create a line of illumination with each of the different wavelengths. The light detection may be applied to authenticate and validate documents, such as banknotes moving along a document conveyer.

21 Claims, 13 Drawing Sheets

(56) References Cited

U.S. PATENT DOCUMENTS

| | | |
|---|---|---|
| 5,418,855 A | 5/1995 | Liang et al. |
| 5,578,813 A | 11/1996 | Allen et al. |
| 5,740,223 A | 4/1998 | Ozawa et al. |
| 5,844,682 A | 12/1998 | Kiyomoto et al. |
| 5,923,413 A | 7/1999 | Laskowski |
| 6,013,912 A | 1/2000 | Pautrat et al. |
| 6,165,609 A | 12/2000 | Curatolo |
| 6,178,227 B1 | 1/2001 | Sato |
| 6,198,835 B1 | 3/2001 | Banton et al. |
| 6,354,507 B1 | 3/2002 | Maeda et al. |
| 6,477,227 B1 | 11/2002 | Kaiser et al. |
| 6,501,825 B2 | 12/2002 | Kaiser et al. |
| 6,563,902 B2 | 5/2003 | Takahashi |
| 6,774,986 B2 | 8/2004 | Laskowski |
| 6,819,409 B1 | 11/2004 | Tompkin et al. |
| 6,909,770 B2 | 6/2005 | Schramm et al. |
| 6,917,040 B2 | 7/2005 | Thierauf et al. |
| 6,918,482 B2 | 7/2005 | Thierauf |
| 7,006,204 B2 | 2/2006 | Coombs et al. |
| 7,030,371 B2 | 4/2006 | Vasic et al. |
| 7,054,461 B2 | 5/2006 | Zeller et al. |
| 7,067,824 B2 | 6/2006 | Muller et al. |
| 7,184,133 B2 * | 2/2007 | Coombs et al. ............ 356/71 |
| 7,215,414 B2 | 5/2007 | Ross |
| 7,218,386 B2 | 5/2007 | Alcock et al. |
| 7,414,710 B2 | 8/2008 | Wunderer et al. |
| 7,487,919 B2 | 2/2009 | Giering et al. |
| 7,529,003 B2 | 5/2009 | Fukawa |
| 7,620,200 B2 | 11/2009 | Rhoads |
| 7,737,417 B2 | 6/2010 | Giering et al. |
| 7,812,935 B2 | 10/2010 | Cowburn et al. |
| 7,912,272 B2 | 3/2011 | Joshi et al. |
| 7,926,730 B2 | 4/2011 | Auslander et al. |
| 8,125,624 B2 | 2/2012 | Jones et al. |
| 8,194,237 B2 | 6/2012 | Cronin et al. |
| 8,229,821 B2 | 7/2012 | Mennie et al. |
| 8,547,537 B2 | 10/2013 | Cronin et al. |
| 2002/0097833 A1 | 7/2002 | Kaiser et al. |
| 2004/0022355 A1 | 2/2004 | Kaiser et al. |
| 2005/0178841 A1 | 8/2005 | Jones, II et al. |
| 2007/0119950 A1 | 5/2007 | Auslander et al. |

FOREIGN PATENT DOCUMENTS

| | | |
|---|---|---|
| EP | 1117060 A1 | 7/2001 |
| EP | 1246876 B1 | 8/2003 |
| EP | 2453382 A2 | 5/2012 |
| WO | 02068945 A1 | 9/2002 |
| WO | 03063096 A1 | 7/2003 |
| WO | 2004052059 A2 | 6/2004 |
| WO | 2004052059 A3 | 6/2004 |
| WO | 2004104947 A2 | 12/2004 |
| WO | 2004104947 A3 | 12/2004 |
| WO | 2004104948 A1 | 12/2004 |
| WO | 2005100926 A1 | 10/2005 |
| WO | 2007025740 A1 | 3/2007 |
| WO | 2011047235 A1 | 4/2011 |

OTHER PUBLICATIONS

Foreign communication from a related counterpart application—European Search Report, European Application No. 10824145.6, Apr. 8, 2013, 9 pages.

Foreign communication from a related counterpart application—International Search Report and Written Opinion, PCT/US2010/052805, Dec. 6, 2010, 6 pages.

Foreign communication from a related counterpart application—International Preliminary Report on Patentability, PCT/US2010/052805, Apr. 17, 2012, 5 pages.

* cited by examiner

CODE1*CODE2 = 0   SIGNAL = A1*CODE1+A2*CODE2+ ... +A12*CODE12
CODE1*CODE1 = 1   DEMODULATE SIGNALS FOR EACH WAVELENGTH:
CODEi*CODEj = 0 | i ≠ j   SIGNAL*CODE1=A1
CODEi*CODEj = 1 | i = j   SIGNAL*CODE2=A2
                  ....
                  SIGNAL*CODE12=A12

| CHANNEL | SENSOR HOUSING | WAVE-LENGTH | MODULATION CODE |
|---|---|---|---|
| 1 | LSH | 690nm | 0100100110111001011100000111111010101011101010000100100 |
| 2 | LSH | 715nm | 1100110100000001010101110001011111001101110101010000100 |
| 3 | LSH | 740nm | 0001110100000011110010011101101110011001011100001111100 |
| 4 | LSH | 770nm | 0110000100100010011111011101010011100101010101000010 |
| 5 | LSH | 810nm | 1010111010000011111001011110101011001001010101010010000 |
| 6 | LSH | 840nm | 1001010000011110001101001101111001111011001010101001010 |
| 7 | USH | 690nm | 0010011110010001101010001111010111001010010100100100 |
| 8 | USH | 715nm | 1000011010101010110111011111000101110110010110010011 |
| 9 | USH | 740nm | 1000100010111101011100010110110110010101001100100010 |
| 10 | USH | 770nm | 0000010101001000011010101101101110000101010011001010 |
| 11 | USH | 810nm | 1001001001011100110110110111111000010101000101001 |
| 12 | USH | 840nm | 0010010101011010010111110010100000101010001110001 |
| 13 | LSH | 880nm | 1100000011000000111010010100010011110000101111000101001 |
| 14 | LSH | 940nm | 0011010000011101101001011110111111010100001010000011 |
| 15 | LSH | 970nm | 0100110011100001011010100100010110110110010100100100 |
| 16 | LSH | 1050nm | 0001011111000001001010101100101010110100101010010001 |
| 17 | LSH | 1200nm | 0000110000011001010101101010111011111011100110100001 |
| 18 | LSH | 1300nm | 0000101010100100110010110000010111011111001010100101010 |
| 19 | USH | 880nm | 0101010001001010000010110110101010011001110101100101111 |
| 20 | USH | 940nm | 0100011000111010100010110111100100111011001011100010 |
| 21 | USH | 970nm | 0110001000100100101011010110110010111010010010101010100 |
| 22 | USH | 1050nm | 1010000101110101001100100101111010110100010101001001100 |
| 23 | USH | 1200nm | 0010100011101110010011001110101010100010101011000 |
| 24 | USH | 1300nm | 0111011001110100111010011011010001100100000010000 |

Fig. 22

OBJECT AUTHENTICATION

CROSS-REFERENCE TO RELATED APPLICATIONS

This application is a continuation of U.S. patent application Ser. No. 13/487,442 which is a continuation of U.S. patent application Ser. No. 12/904,908 issued as U.S. Pat. No. 8,194,237, which claims benefit to U.S. provisional patent application Ser. No. 61/251,915, filed on Oct. 15, 2009, which is hereby incorporated by reference herein.

TECHNICAL FIELD

This invention relates in general to authentication of a document, and more particularly, to characterizing a document from scattered light generated from a multi-spectral light source.

GENERAL INFORMATION

Viewing and analyzing a document with the naked eye is limited by human constraints and human error. Spectroscopy uses light and sensors to view objects that a human cannot see and/or in a manner that a human cannot perform in a reasonable amount of time. For example, for the purposes of acquiring a multi-spectral image of a document, multiple wavelengths of light impinge upon a document. A portion of the incident light may propagate through the document, a portion of the light may be absorbed by the document or its printed inks, and a portion may be scattered back or reflected from the document. Generally, a measurement of the light scattered from the surface of the document is utilized, and may in turn be used to confirm the document authenticity.

A number of methods may be utilized for acquiring a multi-spectral image of a document. In operation, a variety of light sources, filters, selective detectors, and optical arrangements may be used to create proper illumination and imaging conditions for acquiring such data. However, with respect to acquiring images of high-speed moving objects within a confined space, such as on a high-speed document transport device, these methods may face additional challenges. The capture of well-resolved images both spectrally (number of wavelengths imaged) and optically (pixel resolution) begs for a robust arrangement of imaging resources.

One approach for imaging in such moving conditions is line scan (also referred to as "pushbroom") imaging. Line scan imaging uses a one- or two-dimensional sensor to capture a two-dimensional ("2D") image of the moving object. Line scan imaging may be performed by using one or more lines of sensor pixels. In operation, the second dimension results from the motion of the object with respect to one or more detectors, and subsequent "stitching" of the one-dimensional data together is performed to create a composite image. An image of finite length is therefore captured line-by-line by the detector(s) and may be assembled via computer processing.

Another approach to high-speed imaging may include the use of a large two-dimensional array and imaging the target onto that array. Under these conditions, a very bright light source is used to illuminate the entire area, and the image is captured quickly before the motion of the object induces blur or other resolution reducing problems develop. Alternatively, a portion of the array could be used and multiple two-dimensional images could be stitched together to create a single image similar to the "stitching" of a line scan image.

Multi-spectral imaging of an object adds further complexity. For example, for each image taken, the challenges of line scan imaging and two-dimensional imaging may be further complicated by creating images at each light wavelength of interest. For line scan imaging, multiple lines of illumination are created and/or multiple sensors of different spectral sensitivity are implemented to capture images, which are "stitched" together in physical (2D) space, and registered in wavelength space as well. For two-dimensional areas, the utilization of bright illumination and high-speed acquisition are further complicated by having to perform these operations for all wavelengths of interest before the object moves out of view.

In general, there are a number of ways of illuminating a document. Except in the case of transmission illumination, these illumination techniques affect the ability to collect light at the detector or detectors. In general, the space adjacent to a document is shared between the mechanisms for illumination and detection. As this physical space is limited, so too may be an ability to collect and/or illuminate the document being examined.

One technique of illumination is "epi-illumination" in which the light perpendicularly impinges upon the document, and the scattered light from the document travels back along the same path for some distance. This illumination procedure necessitates, to some degree, either blocking some portion of the collected light, or an overall reduction in the total collected efficiency. Techniques utilized for such illumination may be implemented by using partially silvered mirrors or polarizing beam splitters.

Another illumination technique is shared numerical aperture ("shared-NA"), or grazing illumination, where the illumination is incident at an angle to the document, which can limit the collection angle of the optical detection mechanism. "Shared-NA" refers to a process of using the space around a sample and the optics, and the "NA" is the cone of light originating from the field of view and being collected by the optical system. For the most efficient light collection possible, one may desire to use all of this NA light. The less collected light and the less brightness used, the worse the detected signal. The act of "sharing NA" means that a portion of the ability to collect light is sacrificed to illuminate better. Unlike epi-illumination, little or none of the same optical path is shared and hence does not require a "splitting" mechanism. The choice between these two illumination techniques may be determined by the distance to the object and the required optical illumination or collection efficiency.

A document may be illuminated in either a structured or unstructured manner. An example of unstructured illumination is a lamp in which its light directly impinges the document. A problem with such unstructured illumination is its inherent low efficiency, since only a small portion of the source light reaches the document of interest, resulting in significant portion of the light effectively wasted. This inefficiency is undesirable because it may increase power usage, may increase heat (which may lead to many electronic or thermal dissipation problems), and may increase relative noise (less light may mean less signal-to-noise).

Structured illumination, however, is often more efficient at collecting and directing the source light to the document of interest. As a result, less heat is generated, and less power is used to illuminate the document of interest. Multi-spectral imaging often requires multiple, independently-controlled light sources spatially offset from one another. To create equal illumination of the regions of interest in the document, it may be necessary to slightly redirect each illumination source to compensate for this spatial offset, which is generally not possible with a single, unstructured light source.

Solid-state light sources, such as light emitting diodes ("LEDs") or diode lasers, may be used. Structured illumination effectively collects and directs these light sources to the document of interest using the most effective spatial distribution. Depending upon the arrangement of detection optics and detector arrays, different structured illumination distribution schemes might be used to provide an optimal lighting configuration.

Line scan imaging may utilize a single line of structured illumination across the target so that it just "overfills" the area to be imaged by the detection optical system; any greater area of illumination would be lost and an inefficient use of light. One configuration of line scan illumination may be a set of cylindrical optics, which have zero power to condense the light in the extrusion direction, but can have significant optical power in the orthogonal direction. By modifying the power of the cylindrical lens(es), one can control the magnification in the orthogonal direction. For example, a 100 mm long array of 300 micron wide LEDs can form a line of illumination approximately 100 mm long and 3 mm wide if a cylindrical optical configuration of 10× magnification is used. This configuration results in a controlled magnification of the light source in the orthogonal direction while blurring the illumination along the line of illumination. This blurring may be advantageous if different LEDs are placed in a linear array to obtain a more uniform distribution of the light. There are other mechanisms to form a line of light, including commercially available one-dimensional diffusers, when used with collimated light sources, such as lasers.

An optical configuration that images the line of illumination back to the array of detectors may utilize a conventional imaging approach using spherical as opposed to cylindrical lenses. The cylindrical lenses may be used to form the illumination of the sample and not for the imaging aspect.

BRIEF DESCRIPTION OF THE DRAWINGS

FIG. 22 illustrates an example table of modulation codes, according to example embodiments of the present invention.

DETAILED DESCRIPTION

Figure 1:
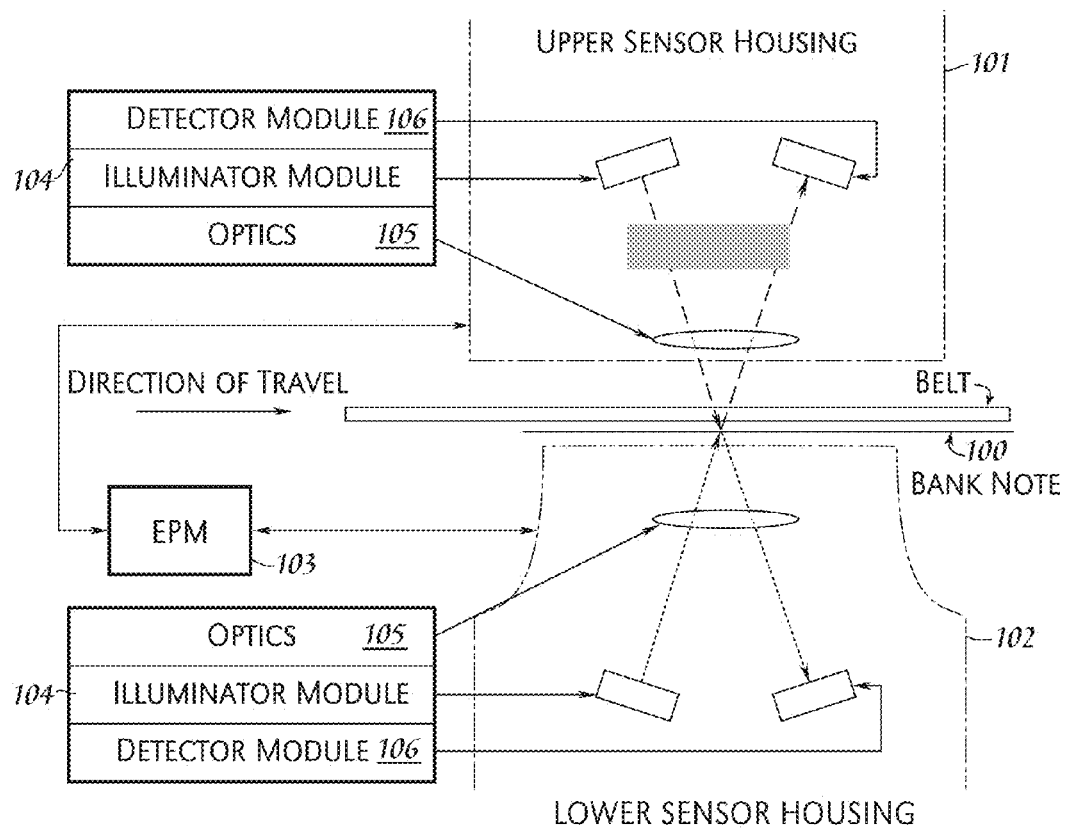
FIG. 1 illustrates an example sensor system, according to example embodiments of the present invention.

It will be readily understood that the components of the present invention, as generally described and illustrated in the figures herein, may be arranged and designed in a wide variety of different configurations. Thus, the descriptions of the embodiments of the present invention, as represented in the figures, is not intended to limit the scope of the invention as claimed, but is merely representative of selected embodiments of the invention.

The features, structures, or characteristics of the invention described throughout this specification may be combined in any suitable manner in one or more embodiments. For example, the usage of the phrases "example embodiments," "some embodiments," or other similar language, throughout this specification refers to the fact that a particular feature, structure, or characteristic described in connection with the embodiment may be included in at least one embodiment of the present invention. Thus, appearances of the phrases "example embodiments," "in some embodiments," "in other embodiments," or other similar language, throughout this specification do not necessarily all refer to the same group of embodiments, and the described features, structures, or characteristics may be combined in any suitable manner in one or more embodiments.

Embodiments of the present invention provide a document authentication sensor that detects features, characteristics, and attributes of documents, including, but not limited to, banknotes and drafts. The remainder of the description exemplifies applications related to banknotes and related examples. However, such image capturing configurations may be applicable to any document, including, but not limited to, identification credentials, security labels, packaging, or any surface that may be authenticated with multi-spectral imaging. Furthermore, embodiments of the present invention are not to be limited to documents, but may be applicable to any target or object that can be imaged in accordance with such embodiments. The image capturing sensor may perform certain operations to determine the presence and/or authenticity of a spectrally unique feature present in banknotes, the denomination of banknotes, and/or the presence of multiple banknotes.

According to example embodiments of the present invention, line scan imaging may be used to produce a line of illumination that is spatially swept relative to an object (e.g., a document) to be characterized, such as for purposes of authentication, and resultant scattered and/or reflected light is then sensed or captured by a linear detector. Due to the relative motion between the optics and the object, multiple sequential line images build up to form the captured image. This configuration provides an ability to form images or multi-spectral image stacks of fast moving items, such as banknotes or manufactured items, such as transported by or on a moving conveyer. The terms "image" and "images" are used herein to refer to data collected as a result of the detection of light energy scattered, reflected, and/or filtered by a target object, which resulted from illumination of the target object by one or more light sources. It is not necessary that such "images" be either visible or displayed on a display device, though for purposes of describing embodiments of the present invention, one or more figures referenced herein may illustrate such an "image" or "images." Herein, the terms "scattered" and "reflected" may be used interchangeably to describe the light received by detectors, emanating from the target object as it is illuminated by one or more light sources. As disclosed herein, an "image" may be comprised of "pixels," which essentially identify a predetermined location of a predetermined size (area) on the object being examined.

A multi-spectral image stack is characterized by a collection of images of the target object of interest, which are collected under different illumination conditions. These different illumination conditions may be characterized by each image generated by scattered light as a result of illumination from a light source of a different wavelength and/or collection of light of different wavelengths.

An approach to overcome the limited spectral bandwidth of a single detector array is to interlace different detectors of different spectral sensitivities in the same array. However, this approach may degrade the overall spatial resolution in the direction of the array. It also requires some degree of interpolation as the different types of detectors are spatially separate from each other.

Another technique may include multiple linear arrays of different types of detectors. In this technique, two (or more) parallel lines of illumination are formed at the sample by two (or more) linear arrays of LEDs. The linear arrays of LEDs may each use a set of cylindrical optics. Similarly, this configuration may be simplified by using only a single set of cylindrical optics, which may result in cost reduction of the illumination optical system, reduced difficulty of alignment, and/or ensuring that the two lines of illumination are parallel and separated by the correct distance.

An alternative technique may include multiple linear arrays with the same type of detector, such as silicon, where each linear array has been filtered, for example, with red, green, and blue filters. This allows for a color image reconstruction, or multi-spectral reconstruction if more than three arrays are used. The use of multiple arrays may allow more image acquisitions to occur in the same periods of time, thus allowing the use of more wavelengths for superior spectral resolution.

Example embodiments of the present invention disclose combinations of optical component arrangements and signal processing to enable high-speed multi-spectral line scan imaging. Examples may include optimized implementations of forming structured illumination by a linear array of LEDs having different wavelengths in accordance with a cylindrical optics illumination.

Example embodiments may provide an illumination configuration that includes a linear array of LEDs, where each of at least a plurality of the LEDs produces a different wavelength of light. Further details of the illumination configuration may include each of at least a plurality of the LEDs being independently controlled (e.g., modulated), or controlled in various sets or groups of multiple LEDs. For example, certain multiples of the same LED wavelength may be uniformly spaced along the array a predefined distance apart. As further described in detail herein, the illumination may be modulated according to a time reference created within the sensor that allows correlation between illumination conditions and the detector output.

As further described in detail herein, on the detection side of the sensor configuration, an arrangement of detector elements may be formed to allow simultaneous imaging of multiple sets of wavelengths to collect a larger set of wavelengths within limited time and space budgets. The structured illumination and detection arrays may be coupled through an optical system that images the multiple sets of wavelengths on the appropriate multiple sets of detection elements. The multi-spectral images may be created from the detector data by "stitching" together the appropriate data based on time references, or another technique, used in the acquisition process to create a spatially and spectrally resolved multi-spectral image stack.

According to example embodiments of the present invention, two linear arrays of LEDs form two lines of illumination at the target document, which are imaged back to two linear arrays of detectors. One line of illumination contains a first set of wavelengths that are sensed by the first array of detectors, and the other line of illumination contains a second set of wavelengths that are sensed by the second array of detectors. By use of time-division multiplexing ("TDM") of the different LEDs, or other illumination techniques such as direct sequence spread spectrum modulation ("DSSSM"), as further described in detail herein, a multi-spectral array of images spanning multiple detector spectral ranges may be formed. The use of additional lines of illumination and arrays of detectors may also be used to further extend the spectral range.

The above-noted approaches to image acquisition may not reduce the lateral spatial resolution that a single array of different interpolated detectors would produce. However, it utilizes a known relative motion, as these arrays of detectors are laterally spaced. To reconstruct the full image, the speed of relative motion and the separation distance between the arrays may be used to digitally "shift" the different linear arrays to be co-linear once each portion has been detected. Therefore, multi-spectral images of high optical and spectral resolution are obtained in a very small form factor.

Referring to FIG. 1, embodiments of a sensor system comprise three subsystems, for example, an upper sensor housing ("USH") 101, a lower sensor housing ("LSH") 102, and an external processor module ("EPM") 103. The external processor module 103 may reside at a remote location, or the EPM 103 may be co-located with the USH 101 and LSH 102.

Authentication operations as well as other imaging-based measurements, such as determination of the note denomination, facing, orientation, etc., may be performed by a back-scatter imaging mode of the sensor system. In this back-scatter mode of operation, light is transmitted from an illuminator module 104, strikes (impinges) a surface of the banknote 100, and reflected light is scattered back into the housing (either or both of the USH 101 and LSH 102), through the optics 105, and onto a housing's detector module 106.

The above-noted procedure of transmitting light towards the banknote 100 may be performed on both sides of the banknote 100 as illustrated in the upper sensor housing 101 and the lower sensor housing 102. The results obtained by the upper sensor housing 101 and the lower sensor housing 102 are forwarded to the EPM 103 for processing. In FIG. 1, the paths traveled by the light waves within the upper sensor housing 101 are generally indicated by the dashed line; the paths traveled by the light waves within the lower sensor housing 102 are generally indicated by the dotted line.

A spatial detector resolution of the sensor system may be limited by the number and spacing of the detection elements (sensors) in the detector module 106, or by the inherent optical resolution of the optics 105, whichever is poorer. For example, a detector spacing of 2 microns center-to-center between the detector sensors may be unnecessary if the optical system has a 100 micron blur spot.

Assuming that an engineered optical design permits a desired detector spacing to be implemented, there are other considerations, such as the speed of the sensor system. For example, existing off-the-shelf detectors/sensors have an advantage of multiple detectors/sensors located within a very small pitch (e.g., on the order of 1 micron), but only have a single or a few read-out element(s) that convert the electrical signals from each of the many detectors/sensors to a stream of digital data. This read-out conversion may have a maximum data rate that limits the overall processing speed of the detector module 106.

Alternatively, a custom detector array may have many digitizing elements, allowing up to one digitizer per element. This significantly increases the throughput of the array, however, these detector elements may be much larger (e.g., on the order of 100-1000 microns). This may significantly limit the spatial resolution. A third alternative is a fully customized detector array, which may have many tiny detector elements (e.g., with a resolution of 10 microns) and many digitizing elements, which allows for both increased processing speed and imaging resolution.

Figure 2:
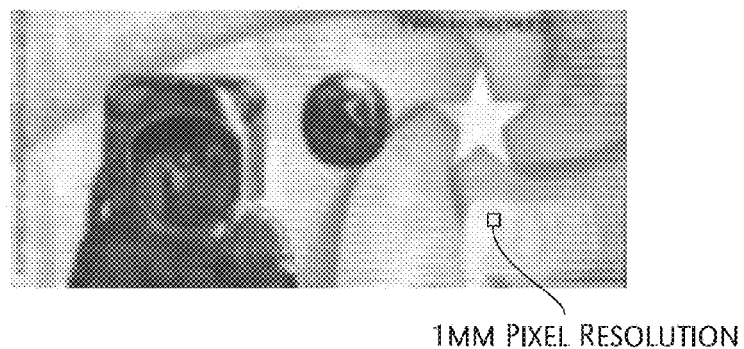
FIG. 2 illustrates an example detected image, according to example embodiments of the present invention.

The back-scattered image collected by each sensor housing 101, 102 may be a multi-spectral stack of two-dimensional images of the surface of the banknote 100 with a predefined resolution (e.g., 1 mm). However, lower and higher resolutions are within the scope of the present invention. FIG. 2 illustrates an example of a banknote 100 sampled with a 1 mm pixel resolution, according to example embodiments of the present invention. The spectral resolution of the detected image may vary depending on various factors. The illumination elements used in the illuminator module 104 may be selected from very narrow optical frequency sources, (e.g., lasers and moderate spectral width sources such as LEDs), or broad optical frequency sources (e.g., lamps).

The spectral resolution may also be controlled through the use of certain detectors included in the detector module 106. The detectors may be selected based on a target light wavelength. One example of such a detector may be a filtered photodiode. Certain filters may be used to allow any set of wavelengths to be passed on to the detector. This spectral resolution may vary over the range of wavelengths to be investigated.

Figure 18:
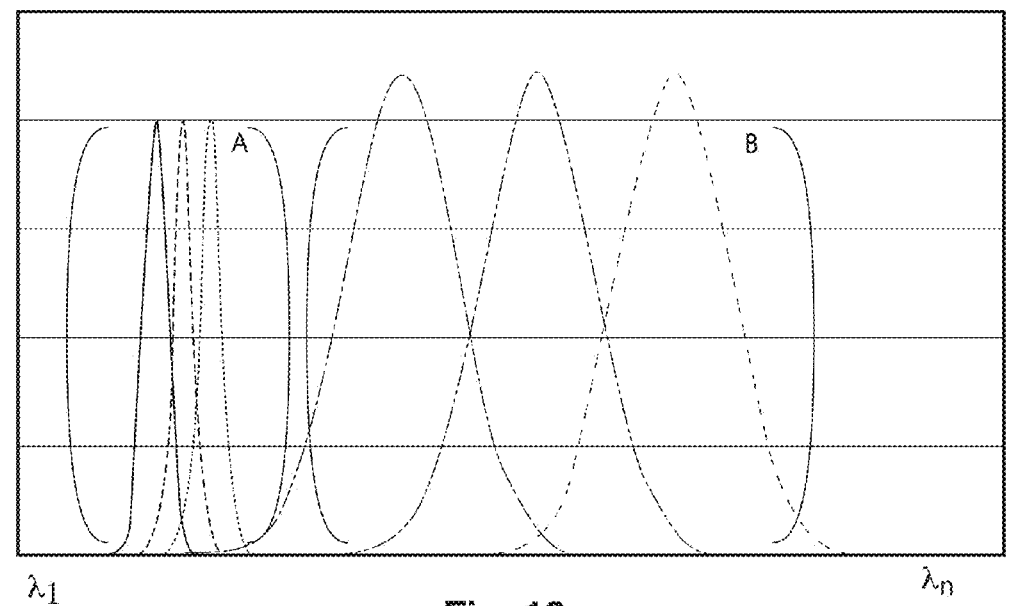
FIG. 18 illustrates an example light wavelength diagram, according to example embodiments of the present invention.

An example of targeted wavelengths is illustrated in FIG. 18, which shows a first set of relatively narrow wavelengths "A" that may be used in the visible region, for example to accurately determine the color of a banknote's ink. A second set of wavelengths "B" of broader frequencies may be used in an infrared ("IR") region to determine an absence or presence of IR transparency.

Figure 3:
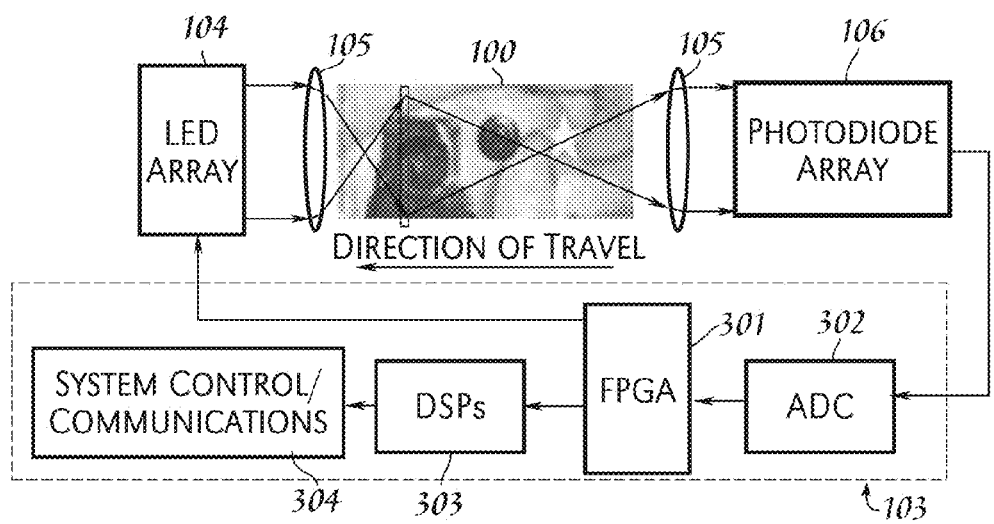
FIG. 3 illustrates an example block diagram, according to example embodiments of the present invention.

Referring to FIG. 3, as noted above with respect to FIG. 1, the upper and lower housings 101 and 102 each include an illuminator module 104, which may include one or more LED arrays and accompanying LED modulators, a detector module 106, which may include one or more imaging arrays and accompanying photodiodes/amps, optics 105, and demodulators and data transmitters (not shown), which feed data to the EPM 103. The EPM 103 comprises one or more field programmable gate arrays ("FPGAs") 301, one or more digital signal processors 303, and a communications processor 304. Modulation codes are generated inside the FPGA 301. The intensity of each set of LEDs can be adjusted individually by way of a digital-to-analog converter ("DAC") (not shown).

The FPGA 301 may also be accompanied by amplifiers (not shown) and an analog-to-digital converter ("ADC") 302 for the photodiode channels contained on the detector modules 106. The FPGA 301 provides oversampling, filtering, and demodulation of the photodiode signals to maximize the signal-to-noise ratio. The FPGA 301 receives the resulting digital values and presents it to the DSP 303 in a format suitable for DSP access. The DSP 303 processes the data using embedded algorithms, such as discussed herein, and may make decisions based on pass/fail criteria and may authenticate the banknote 100. The communications processor 304 may gather results from the DSP 303 and format this data into a message for output.

Figure 4:
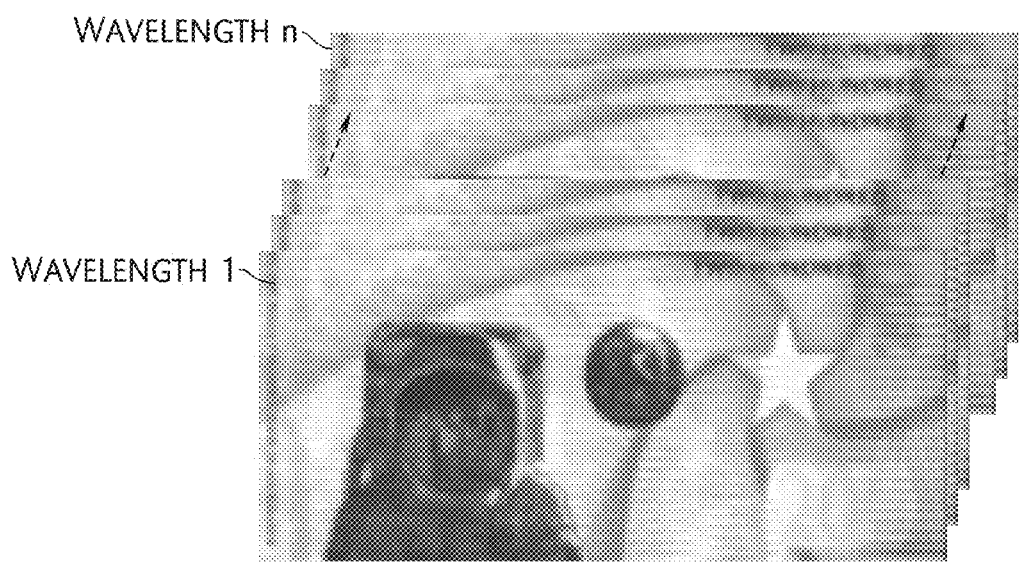
FIG. 4 illustrates an example set of images, according to example embodiments of the present invention.

In embodiments of the present invention, as the banknote 100 travels along a note transport system (which are well-known in the art; see "Belt" and "Direction of Travel" in FIGS. 1 and 3), the illuminator module 104 may illuminate one or both sides of the note 100 with one or more arrays of LEDs included in the illuminator module 104. The scattered light may be captured by the photodiodes of the imaging arrays of the detector module(s) 106. A modulation of the LED wavelengths may be implemented to enable the sensor device to separate the captured image into individual wavelength components. This results in a multi-spectral image stack of "multiple images," which may be analyzed using statistical methods, such as digital filtering and optimum statistical detection, estimation, and classification (or "pattern recognition") methods, or another analysis technique, such as principal component analysis ("PCA") to determine if the identified multi-dimensional reflectance images fall within an acceptable range of variation for authentic banknotes, thereby validating the authenticity of the banknote 100. A statistical analysis of the multi-spectral image stack may also be used to determine the denomination of the note based on spatially separated regions of IR transparent inks and image elements of the note. An example of such a multi-spectral image stack for the example banknote of FIG. 2, imaged with multiple wavelengths is illustrated in FIG. 4. Each of the multiple images 1 . . . n represents an image captured from the light scattered by the banknote 100 at a particular wavelength of light.

Figure 5:
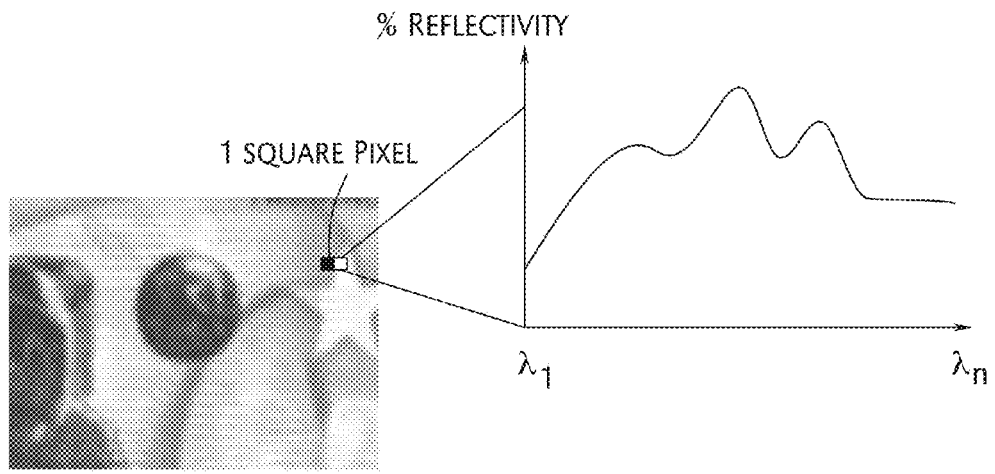
FIG. 5 illustrates an example pixel and wavelength diagram based on an examined document, according to example embodiments of the present invention.

Referring again to FIG. 1, the illuminator module 104 may comprise an LED array that includes a plurality of different LEDs, which provide for a continuous illumination over a broad spectral range. One possible spectral range of interest may be examined by spanning from the ultraviolet to the near infrared by including LED wavelengths from 300 nm to 1700 nm. The LEDs may vary in light wavelengths, by including two, three, or more different LEDs, each having different wavelengths. Example embodiments of the present invention are not limited to such spectral ranges, but may be implemented with any number of wavelengths and detectors of suitable spectral responses. Each pixel from each layer of the multi-spectral image stack (see FIG. 4) represents the intensity of light scattered from the surface of or transmitted through the banknote 100 from a single illumination element. By collecting the intensity from the same spatial position from each layer of the multi-spectral stack, the spectral information is obtained as depicted in FIG. 5.

Figure 7:
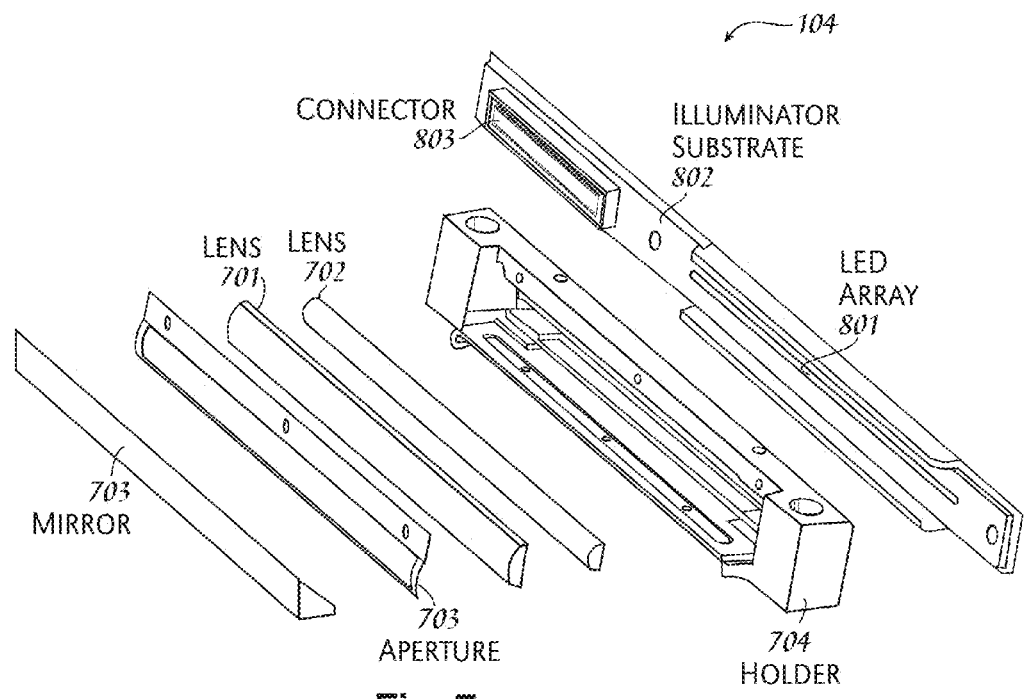
FIG. 7 illustrates an example configuration of an illuminator module, according to example embodiments of the present invention.

FIG. 7 further illustrates components of the illuminator module 104, according to example embodiments of the present invention. The illuminator module 104 comprises a bank of LEDs positioned to project light onto the banknote 100 using a minor and optical lens in optics 105. The LEDs may project a plurality of different wavelengths. The first bank of LEDs may project a shorter wavelength spectrum, and the second bank a higher wavelength spectrum. The LEDs may be modulated using DSSSM or TDM techniques, or any of the other techniques described herein, allowing for simultaneous measurement of multiple wavelengths.

The illuminator module 104 comprises an illuminator substrate 802, a signal connector 803, and an array of LEDs 801 positioned to project light using the optics 105, which with respect to the illuminator module 104 comprises a mirror 703 and two optical lenses 701 and 702. A holder 704 and an aperture 703 may be also part of the illuminator module 104. When the bare LEDs 801 are powered, light passes through the lenses 701 and/or 702. Light is then redirected onto the banknote 100 by the angled minor 703 where it strikes the surface of the banknote 100 and is scattered back into the housing(s) 101 and/or 102, through the optics 105 pertaining to the detector module 106, and onto the detector module 106 (see also FIG. 1).

Figure 8:
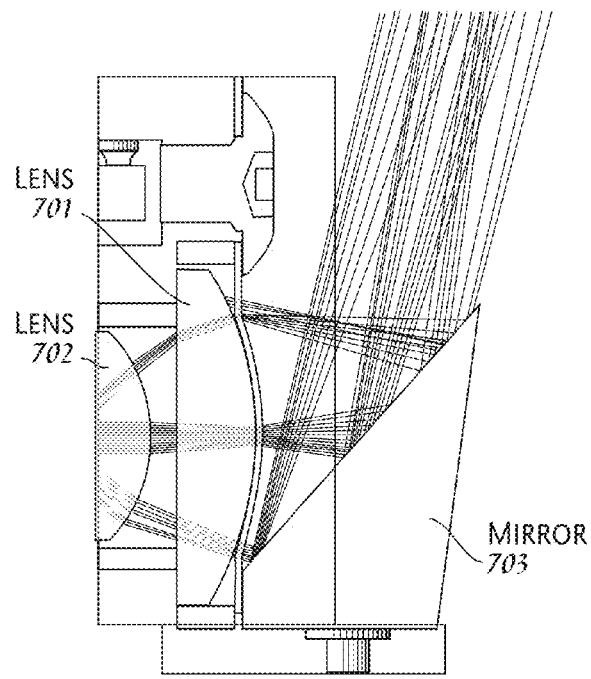
FIG. 8 illustrates example paths of light traveling through an illuminator module, according to example embodiments of the present invention.

An enlarged view of the portion of the optics 105 controlling the light from the illuminator module 104 is illustrated in FIG. 8. As light (represented in the figures as multiple beams) passes through the lenses 702 and 701, the light strikes the mirror wedge 703 and is projected onward to impinge upon the banknote 100. This configuration enables "mixing" of LED illumination for a relatively uniform line of light. The lenses 701 and 702 collect and focus a large portion of the emitted light from the LEDs, and project that light off of mirror 703 to image the array of emitted light upon the target. The cylindrical optics are "1D" optics in the sense that the light is collected and focused in one direction (e.g., see the ray trace exiting out of lens 701), but allow the LED light to spread out and propagate in an orthogonal direction.

Figure 9:
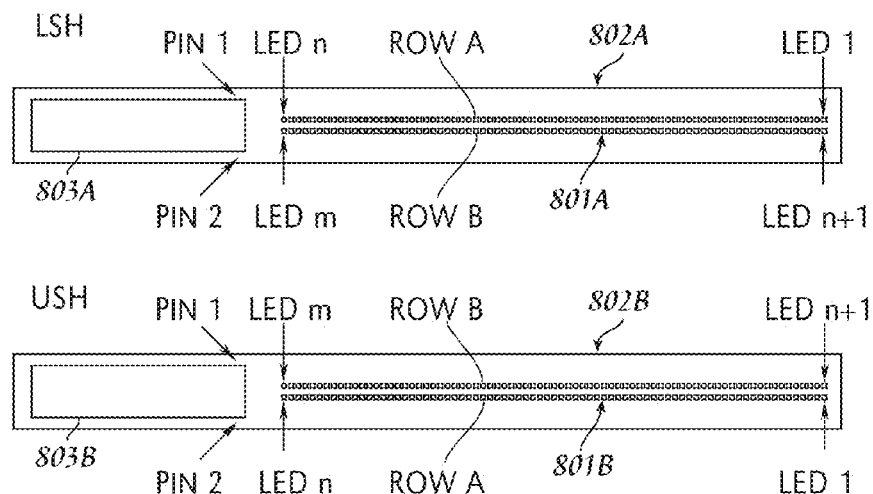
FIG. 9 illustrates an example LED array configuration, according to example embodiments of the present invention.

Referring to FIG. 9, an example of an illuminator module 104 may comprise a substrate comprising two rows of "n" number of bare LED dies 801, with Row A comprising LEDs 1 . . . n, and Row B comprising LEDs n+1 . . . m. Row A and Row B include LED wavelengths from two different spectral regions. The LED array 801 may comprise an array of 12 different wavelengths, a mixture of 7 in Row A that are imaged on one detector array, and a mixture of 5 in Row B imaged on the second detector array. The different LEDs are identified by the wavelength of light they produce. Separate versions of the illuminator module substrate 802A and 802B are utilized for the lower sensor housing (LSH) 101 and the upper sensor housing (USH) 102, respectively. One difference between the two versions may be that one is effectively a mirror image of the other. For example, Row A and Row B of LED array 801A and the signal connector 803 even-pin and odd-pin signals may be swapped (note that LED 1 begins on the top of the illuminator module substrate 802A, and LED 1 begins on the bottom of the illuminator module substrate 802B) with respect to the LED array 801B.

Figure 10:
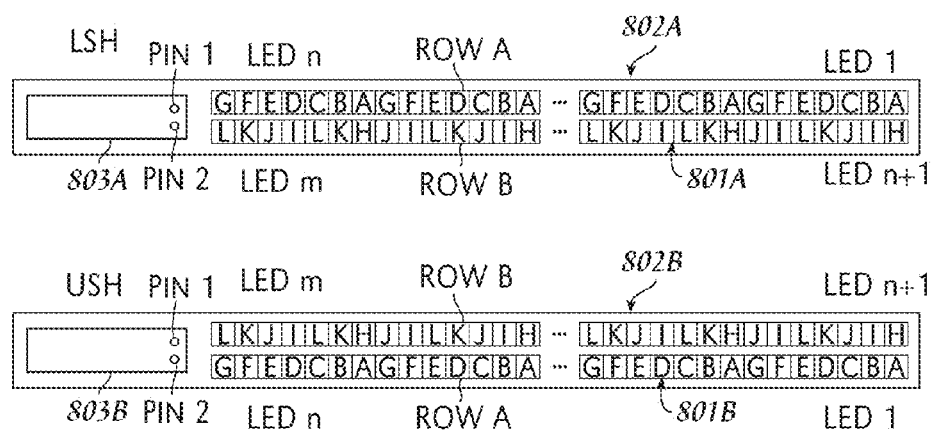
FIG. 10 illustrates an example LED array configuration, according to example embodiments of the present invention.

FIG. 10 illustrates a similar view of the LED arrays 801A and 801B on substrates 802A and 802B, respectively, according to example embodiments of the present invention. Referring to FIG. 10, the LEDs within each Row A and Row B may be evenly distributed in an interleaved pattern to provide uniform, broad-band illumination across the width of the banknote being examined. Each letter represents a different wavelength. This example shows a configuration where in Row A, 7 wavelengths are repeated, while in Row B, 5 wavelengths are repeated. However, one could utilize as many or few wavelengths in either row as needed. In this example, since there are 7 wavelengths in Row A and 5 in Row B, but the same total number of LEDs in both, the wavelengths in Row B have more population per wavelength then those in Row A. If there is a particular banknote feature or set of wavelengths that are to be illuminated brightly, a row with fewer wavelengths (as few as a single wavelength) may be utilized to increase the intensity of that particular color. Likewise, a row where not all the wavelengths were evenly distributed may be utilized, so a row like Row A, but where A=D and therefore that wavelength is double the others. Thus, there would be a total of 7 wavelengths with "A" being populated two times ("2×") as much as the other 6.

Referring again to FIG. 1, each of the housings 101 and 102 may further include a multi-lens optical system (as further described herein) within optics 105 with a photodiode detector module 106, in accordance with example embodiments of the present invention. The optical system focuses the scattered light from the banknote 100 onto an array of photodiodes located within the detector module 106. The photodiodes convert scattered light to an electrical signal that is then used for image processing by the EPM 103, such as to determine the location of certain banknote features. There may be two separate bands of light being used to examine the banknote 100. Short wavelengths may be focused onto one row of photodiodes, and long wavelengths may be focused onto a second row of photodiodes. The light received from each pixel (location of interest) of the banknote 100 is focused onto a single photodiode.

Figure 11:
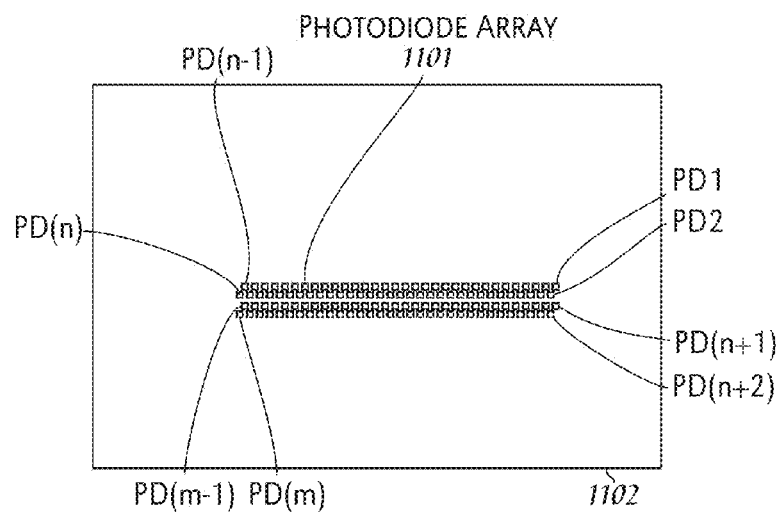
FIG. 11 illustrates an example detector configuration, according to example embodiments of the present invention.

FIG. 11 illustrates a photodiode arrangement of the detector module 106, according to example embodiments of the present invention. Referring to FIG. 11, an example of a detector module 106 may include a photodiode array 1101 mounted on a substrate 1102, which includes a plurality of photodiode sensors PD1, PD2, . . . PD(n−1), PD(n) (first spectral row) and PD(n+1), PD(n+2), . . . PD(m−1), PD(m) (second spectral row). In addition to the sensors, associated trans-impedance amplifiers (not shown) may also be coupled to the sensors to convert the detected light signals to electrical voltage signals. The photodiode array 1101 may be arranged in two "spectral" rows of photodiodes. The first spectral row may be populated with silicon (Si) photodiodes for detecting shorter wavelength light, and the second spectral row may be populated with indium gallium arsenide (InGaAs) photodiodes for detecting longer wavelength light. However, other variations of photodiodes and similar sensors may be used to capture light used in the sensor detection configuration. Additionally, a third row, or additional rows, may further be added to detect yet other wavelengths of light received.

Referring again to FIG. 1, each sensor housing 101 and 102 may utilize a separate version of the detector module 106. The lower sensor housing 102 may comprise InGaAs photodiodes installed at photodiode locations PD1-PD(n) of FIG. 11. Similarly, Si photodiodes may be installed at photodiode locations PD(n+1)-PD(m) of FIG. 11. The upper sensor housing 101 may reverse the order from the lower sensor housing 102, with Si photodiodes installed at locations PD1-PD(n)

and InGaAs photodiodes installed at locations PD(n+1)-PD (m). However, similar variations not shown in FIG. 11 may also be used to arrange the photodiodes.

Figure 12:
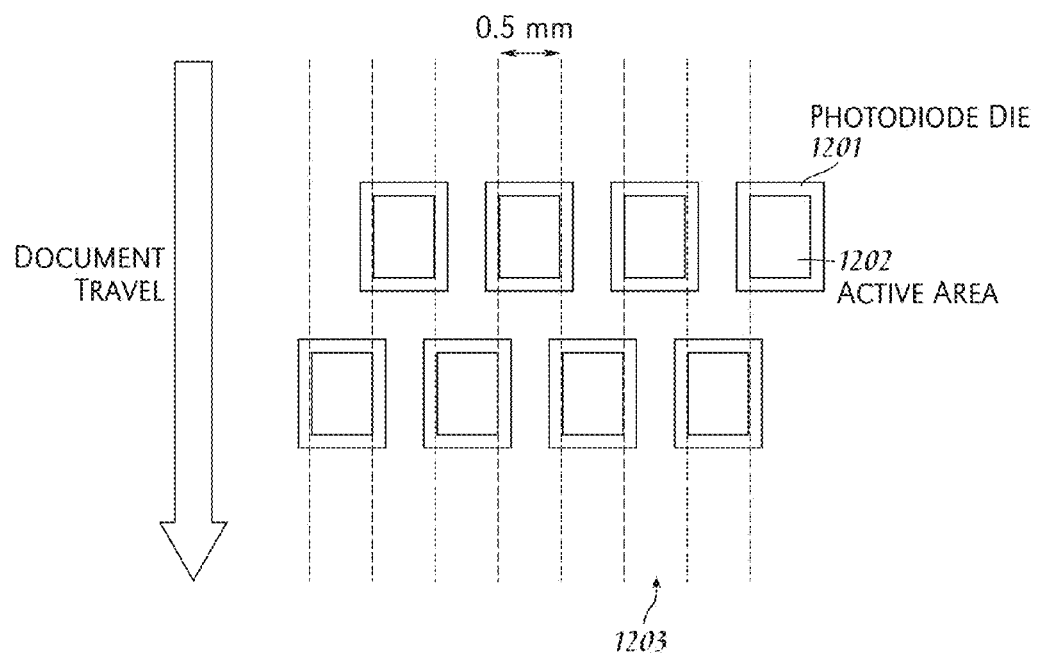
FIG. 12 illustrates an example detector layout, according to example embodiments of the present invention.

FIG. 12 illustrates a spacing configuration for each spectral row of the photodiode array 1101, according to example embodiments of the present invention. Referring to FIG. 12, each photodiode die 1201 has an "active area" 1202 that is smaller than the physical die size 1201. The photodiodes used on the detector module 106 may have active areas that are approximately 0.5 mm wide. Light falling outside the active area may not be converted to an electrical signal, so if the photodiode dies 1201 are placed adjacent to each other within a single row, the portion of the banknote 100 that falls between the active areas of adjacent die 1201 will not be imaged. To alleviate this effect, the photodiodes 1201 within a spectral row may be staggered (offset) as illustrated in FIG. 12. The gaps 1203 between photodiode active areas along the line perpendicular to the banknote travel may be effectively eliminated by the offset layout of the photodiodes 1201.

Figure 13:
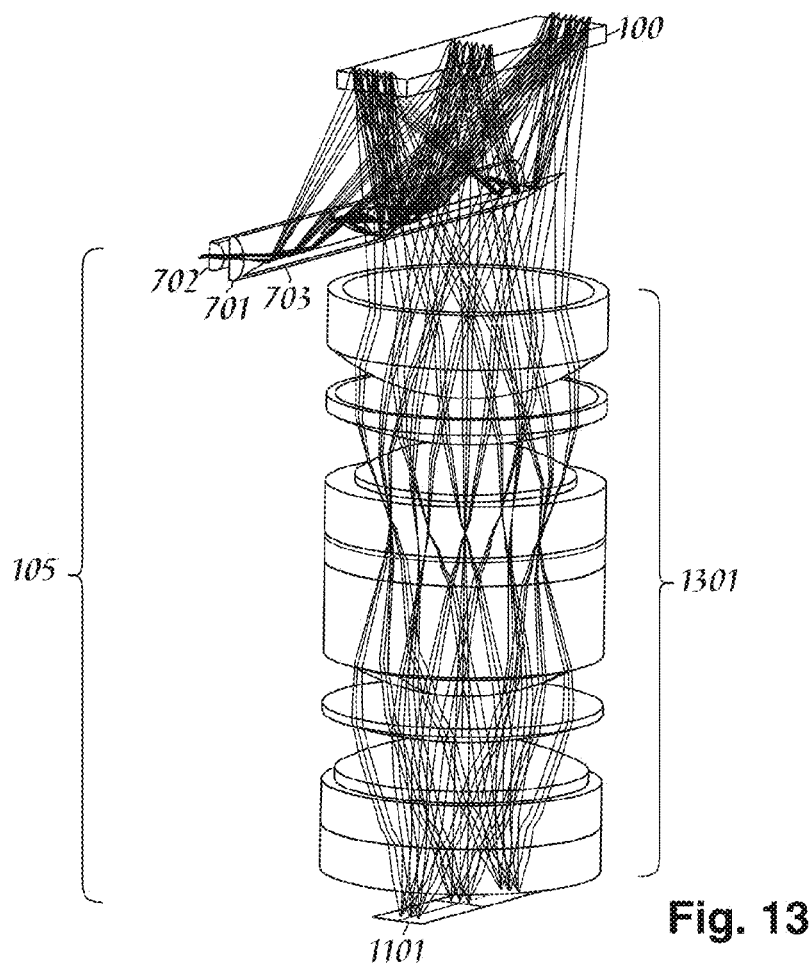
FIG. 13 illustrates an example optics barrel, according to example embodiments of the present invention.

FIG. 13 illustrates an example of the optics 105, according to example embodiments of the present invention. The optics 105 include the illuminator module 104, lenses 701, 702, and minor 703, plus the lens assembly 1301 in the detector module 106. Exemplary light rays are illustrated to depict how the paths of light travel within the system. Optics 105 may include an optics barrel with a machined aluminum housing (not shown) for installation of a detector lens assembly 1301 with precise external surface(s) that locate the lens assembly 1301 within the optical imaging device and provide the capability to focus the assembly for increased performance.

The detector lens assembly 1301 may comprise a relay lens optical system that images the target 100 (banknote) to the detector array 1101 with a high degree of light collection efficiency. The lens assembly 1301 may contain an array of 5 individual lenses and 3 doublet lens assemblies with anti-reflection coating for maximum transmission in the wavelength region. The set of lenses may be chosen to perform the reimaging across a wide range of wavelengths. Optical magnification may be selected based on the resolution requirement for the banknote and the size of detector element. To resolve a feature size of 1 mm on the banknote and for a detector element of 0.5 mm×0.5 mm, a 0.5× optical magnification is utilized. As an example, if the lens assembly provides an optical power of 0.5×, then each 1 mm×1 mm area on the banknote plane is imaged onto a 0.5 mm×0.5 mm area on the detector array 1101 (0.5× means a 1 mm×1 mm area on the banknote shows up as a 0.5 mm×0.5 mm area on the detector plane).

Figure 14:
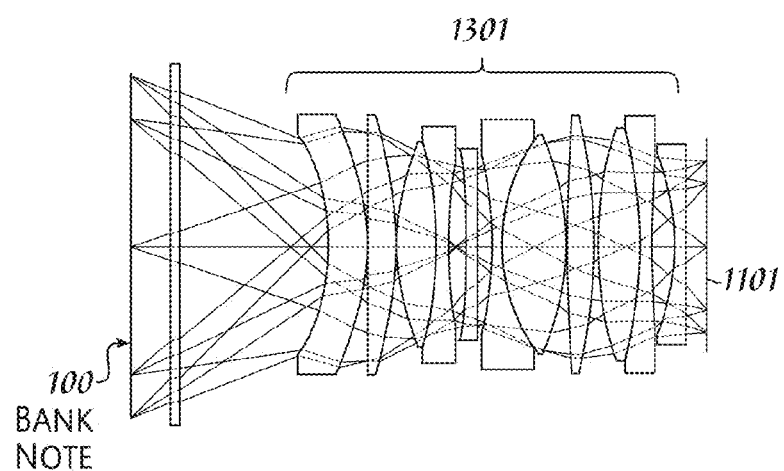
FIG. 14 illustrates an example light ray trace, according to example embodiments of the present invention.

FIG. 14 illustrates an optical system pictorial of a ray trace (ray tracing is a method for calculating the path of waves or particles through a system), according to example embodiments of the present invention. Referring to FIG. 14, details are illustrated five exemplary paths of light contacting the banknote 100 and scattering backwards towards the photodiode detector array 1101. Not all points of interest of the banknote 100 are illustrated in the ray trace of FIG. 14. The barrel casing is not shown in this drawing.

Figure 15:
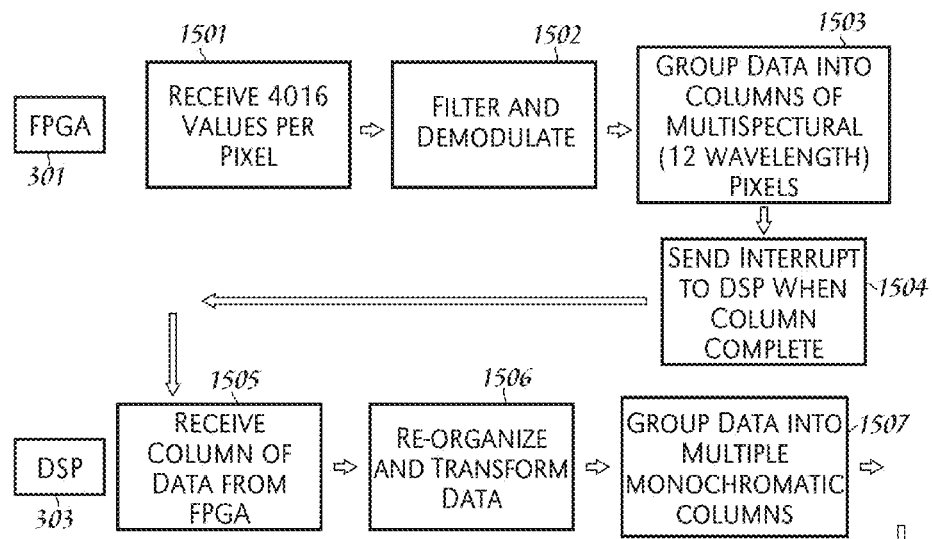
FIG. 15 illustrates an example flow diagram, according to example embodiments of the present invention.
Figure 16:
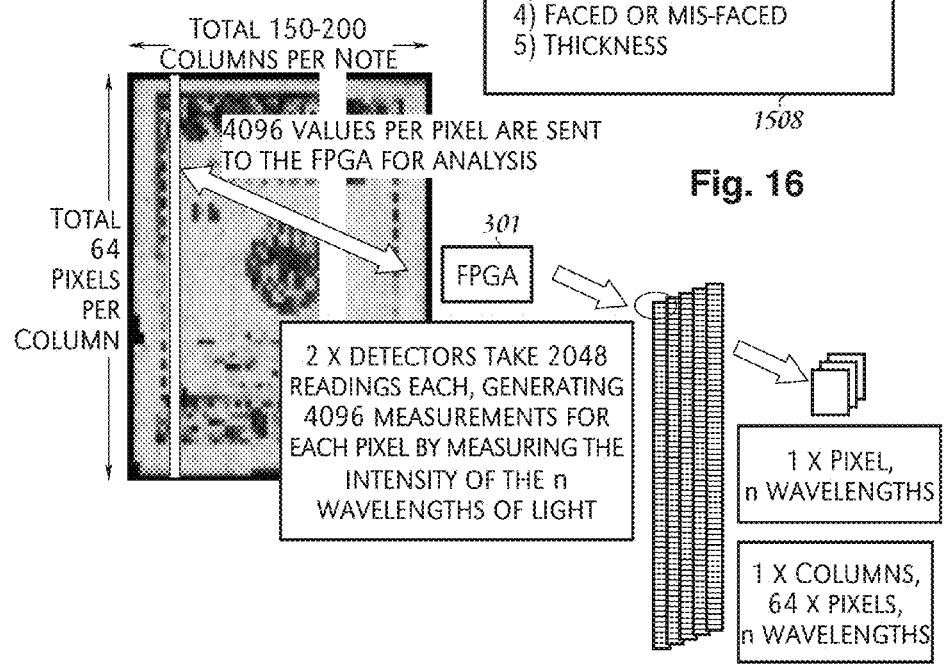
FIG. 16 illustrates an example image data organization configuration, according to example embodiments of the present invention.

FIGS. 15 and 16 illustrate data processing on the raw banknote images (the multi-spectral data) collected by the detector module 106. FIG. 15 illustrates steps performed by the FPGA 301 and DSPs 303, while FIG. 16 provides a pictorial view of how the raw image data is organized by the FPGA 301. With reference to the previous examples for pixel resolution and the number of illuminating wavelengths, two detectors measure the intensity of light for each pixel and generate 2048 readings, which results in 4096 readings per pixel.

The 4096 values of pixel data are received and fed into a FPGA 301 at operation 1501. At operation 1502, the FPGA 301 takes the pixel data, and, using mathematical analysis for filtering and demodulation, a multi-wavelength spectrum is estimated, i.e., light intensities are estimated for each of the individual illumination wavelengths. The FPGA 301 stores multi-spectral column data in an internal dual-port RAM grouped into columns of multi-spectral pixels (i.e., 12 wavelengths) at operation 1503. An interrupt is sent to the DSP 303 when each column is completed at operation 1504. The column data is received at DSP 303 at operation 1505, and the data is re-organized and transformed at operation 1506. The data is grouped into multiple monochromatic columns at operation 1507, and the DSP 303 may run certain algorithms discussed herein to process the data at operation 1508.

Regarding the light measurements, the first part of a document measurement may be a primary surface measurement employing a digital signal processing technique, such as direct sequence spread spectrum modulation ("DSSSM") or time division multiplexing ("TDM"). Once the raw signal of the primary surface measurement is processed in this manner, the image analysis algorithm may employ statistical analysis to determine if any of the identified multi-dimensional reflectance images falls within an acceptable range of variation for authentic banknotes.

The signal processing of the primary surface measurement relates to the control (e.g., modulation) of the LED illuminators and the corresponding analysis of the captured scattered light. This primary surface measurement algorithm relies on the illuminator module 104 and the detector module 106 in the optical front end of the sensor device instrument. A succession of these measurements from each photodiode on the array produces data from which a multi-spectral image may be constructed. This algorithm produces the basic light measurement on a per pixel basis for each wavelength of LED. FIG. 4 illustrates the various different wavelength-based images generated for "n" wavelengths.

A primary surface measurement algorithm has certain performance objectives, such as, to allow multiple wavelength measurements from each unfiltered photodiode and to provide high gain in the raw signal-to-noise ratio ("SNR"). The algorithm allows simultaneous measurement of multiple wavelengths on unfiltered photodiodes by using one of the aforementioned techniques. However, a limitation of many detectors is their limited wavelength range of sensitivity.

For embodiments of the present invention, the sensor may be operated for detection of wavelengths in a range of about 190 nm to 2600 nm range. Since single photodiodes with adequate quantum efficiency across this band are not available, two types of photodiodes may be used. For example, silicon (Si) detectors have a sensitivity range from approximately 190 nm to 1100 nm, though this range can be slightly varied using different doping or coating strategies. Similarly, indium gallium arsenide (InGaAs) detectors may be used, which have a spectral sensitivity from approximately 800 nm to 2600 nm, though this spectral range can also be slightly varied using various strategies. For the described embodiments, silicon (Si) photodiodes may be used for shorter wavelengths, and indium gallium arsenide (InGaAs) photodiodes may be used for longer wavelengths. The detector lens assembly 1301 may be used to focus the scattered light from 1 mm square pixels across the width of the banknote 100 onto an array of photodiodes on the detector module.

The illuminator LED array 801 projects bands of broadband light across the banknote 100, and the scattered light is converted by an array of photodiodes 1101 into electrical signals that are processed, such as for detecting authentication features. Photodiodes are broad-band detectors and are not capable of determining the contribution of each of the wavelengths present in the broad-band illumination.

The illuminator LED arrays 801A, 801B may then comprise two rows of 168 LEDs (see FIGS. 9 and 10). One row (e.g., Row A) may include LEDs of 7 types, to operate as the illumination source for the Si photodiode array. The other row (e.g., Row B) may include LEDs of 5 types, to operate as the illumination source for the InGaAs photodiode array. The different types of LEDs in each row are interleaved to provide a uniform-distribution broad-band light source (see FIG. 10).

To allow wavelength discrimination, the sensor may implement time division multiplexing ("TDM"). TDM processing may implement a rapid sequential illumination of the different LED wavelengths while simultaneously acquiring images with the detectors based on the same time reference used for the original illumination modulation to essentially "freeze the note," wherein the document (e.g., a banknote, or note) does not travel far between subsequent wavelength illuminations. These acquisitions may be taken at speeds sufficient to eliminate significant spatial displacement between exposures. Such a sequence of acquisitions may build a multi-spectral stack of images that represents the same spatial features at each discrete wavelength.

Figure 21:
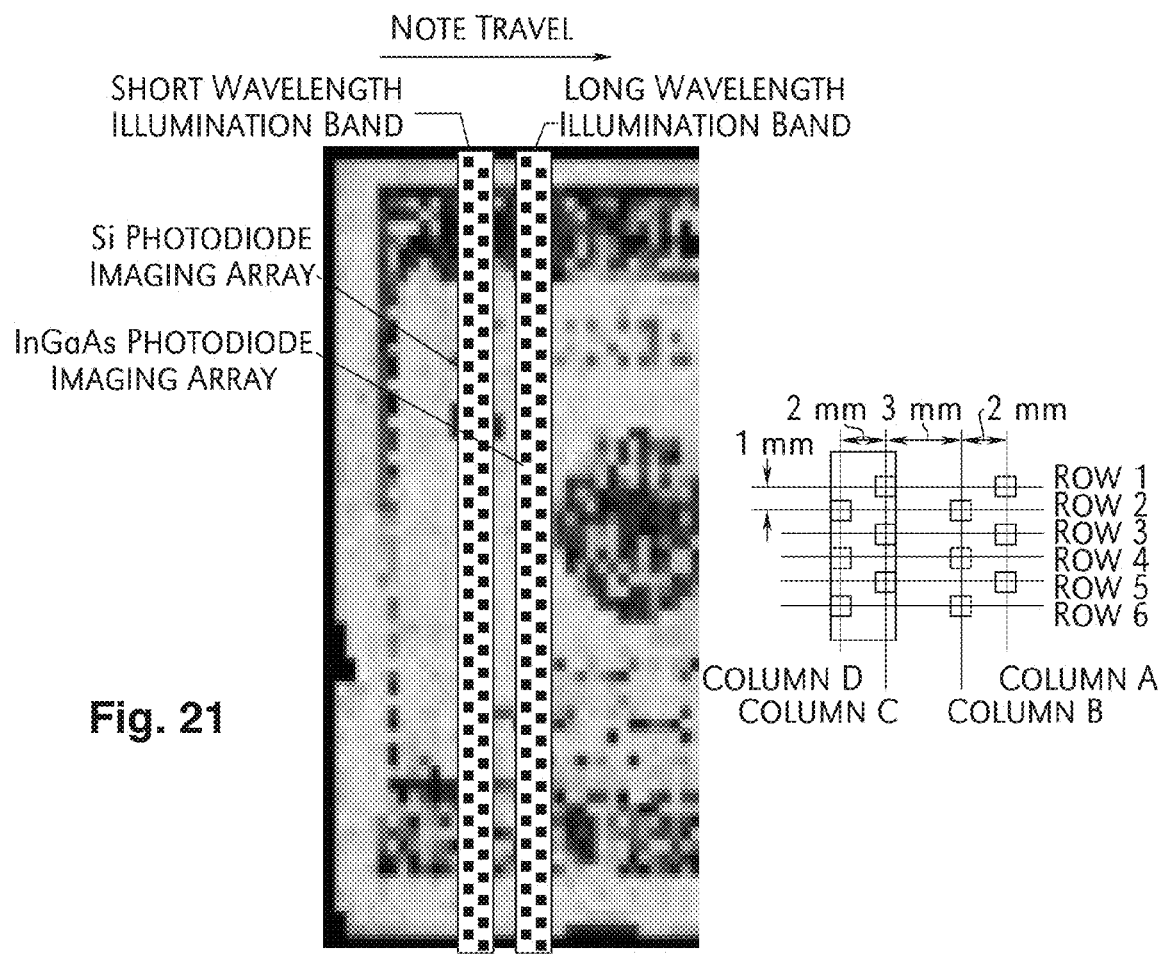
FIG. 21 illustrates an example of multiple illumination bands used to produce images of a document, according to example embodiments of the present invention.

FIG. 21 illustrates illumination bands and pixels that may be imaged by the photodiode array 1101 overlaid on a banknote image. The photodiodes 1201 are arranged in "staggered" rows due to the photodiode physical package mounting constraints, as previously described with respect to FIG. 12. As the note travels across the face of the sensor, the photodiodes image a given feature (pixel) in a time-shifted manner:

Si photodiodes in Column D image a feature at time="N"
Si photodiodes in Column C image a feature at time="N+200 microseconds" (e.g., corresponding to 2 mm of banknote travel time)
InGaAs photodiodes in Column B image a feature at time="N+500 microseconds" (e.g., corresponding to 5 mm of banknote travel time)
InGaAs photodiodes in Column A image a feature at time="N+700 microseconds" (e.g., corresponding to 7 mm of banknote travel time)

The FPGA 301 collects the digitized photodiode voltages and time-aligns them to present coherent columns of pixel data to the DSP 303 for signal processing, as previously described.

Referring to FIG. 22, each LED wavelength may be assigned an orthogonal digital code comprised of a sequence of 64 characters, where each character is a "0" or a "1." Each character in the code represents an interval of time, known as a "chip." A given wavelength is turned on during the chip time if the wavelength's code character for that chip time is a "1." The entire 64-bit code may be repeated for each 1 mm of note travel, which results in a chip equivalent to 1.56 microseconds (i.e., 64 chips occur during the 100 microseconds that it takes for the note to advance 1 mm).

A unique code may be used for each of the 12 illumination wavelengths (though other numbers of wavelengths may be implemented) in the upper sensor housing (USH) 101 and the lower sensor housing (LSH) 102. Unique codes may be assigned to similar wavelengths in the upper and lower sensor housings to allow discrimination of back-scatter mode and transmission mode wavelengths as detailed in the table shown in FIG. 22, which provides an example of codes assigned to the illumination wave lengths. For example, the code assigned to the 940 nm wavelength for the upper sensor housing (USH) 101 (channel 20) is different from the code assigned to the 940 nm wavelength in the lower sensor housing (LSH) 102 (channel 14).

Figure 23:
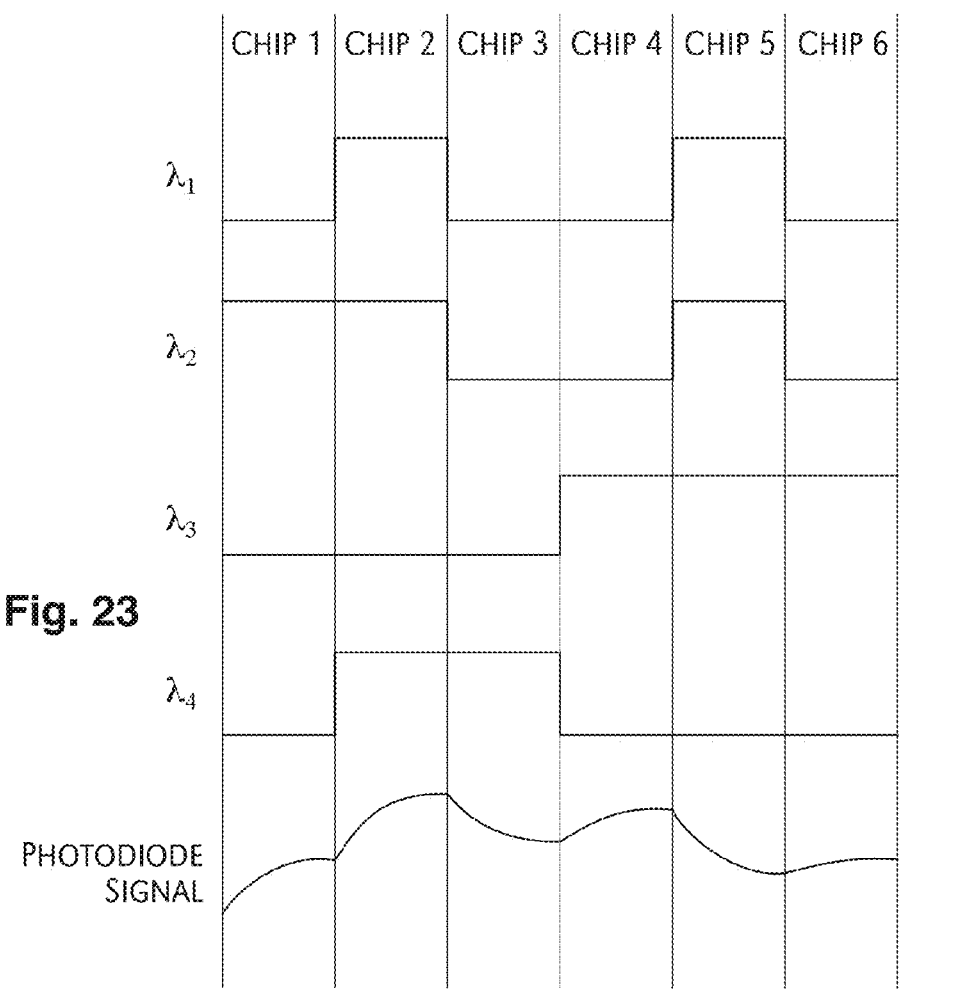
FIG. 23 illustrates an example photodiode signal, according to example embodiments of the present invention.

Referring to FIG. 23, as the codes change from one chip to another, some number of LED wavelengths are turned on and others are turned off. The optical signal at the photodiode may increase or decrease on chip boundaries, depending on the number of wavelengths being turned on and off and the absorption characteristics of the banknote surface. FIG. 23 depicts four example wavelengths $\lambda_1 \ldots \lambda_4$ through six chip intervals and the resultant photodiode electrical signal, which is sent on to be processed by the EPM 103.

Figure 24:
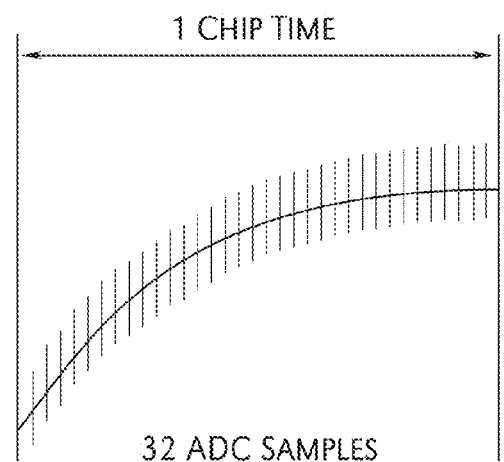
FIG. 24 illustrates an example photodiode signal, according to example embodiments of the present invention.

Referring to FIG. 24, each photodiode signal may be sampled by an analog-to-digital converter ("ADC") 32 times per chip interval. The intensity value for the imaged pixel is calculated from the 32 samples, using an optimal estimation filter. Sampling each photodiode output 32 times per chip interval and using 64 chips per pixel results in approximately a 27 dB increase in signal-to-noise ratio.

With respect to DSSSM for use in wavelength discrimination, each wavelength is assigned a unique code to simultaneously modulate all of the LEDs (all wavelengths) according to their respective codes, and demodulate the resulting combined signal to recover the portion of the signal due to each separate LED wavelength. (For TDM, each wavelength is assigned a different successive time slot, so that they are turned on one at a time.) The signal resulting from a given wavelength being turned on is due to only that wavelength. Regardless of the modulation technique used, the entire sequence is repeated for each pixel worth of note travel (e.g., 1 m or 100 microseconds). For DSSSM, the codes may be a sequence of 32 or 64 "1's" and "0's" (on/off intervals). All 32 or 64 of these intervals occur within the pixel time. (For TDM, all of the time slots occur within the pixel time.)

Figure 6:
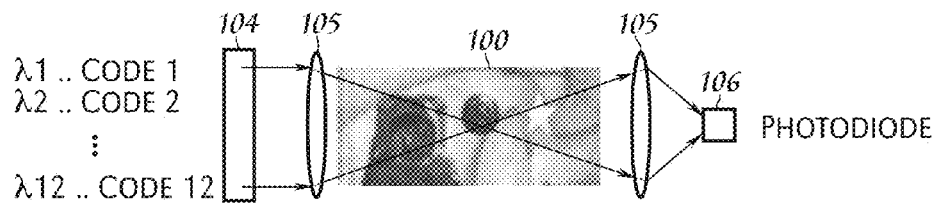
FIG. 6 illustrates an example light concentration and related calculation used to produce a detected image, according to example embodiments of the present invention.

DSSSM historically has been used by the U.S. military for low probability of intercepted communications, but in this application it is used to multiplex spectral data. Referring to FIG. 6, which shows an LED array of the illuminator module 104, the optics 105, and a photodiode of the imaging array detector module 106, the activation of each LED is modulated using DSSSM modulation functions that are mutually orthogonal. This allows all of the LEDs to simultaneously interact with the surface under test and thus produce light signals that are simultaneously received by each of the photodiodes while still allowing the signals from each individual LED wavelength to be electronically separated from the others. In effect, this is a spectroscopic measurement that does not require filters or diffractive elements, of which wavelengths of light fall onto each receiving detector (this is also true with respect to embodiments of the present invention utilizing TDM for this purpose). In operation, each source of light (e.g., LED) generates a different wavelength $\lambda_1$, $\lambda_2$, $\lambda_3$, ... $\lambda_n$, with a corresponding code, code 1, code 2, code 3, ... code n. The "codes" are on/off LED current modulation functions, which may be represented as binary sequences, i.e., sequences of "0's" and "1's." The codes are designed such that they have the same length (n), the same sum (n/2), and are mutually orthogonal, i.e., for any i, j, code(i)*code(j)=n/4. Because of the orthogonality of the codes, the combined light signal is demodulated using the same codes to obtain the portion of the combined signal due to each separate LED wavelength.

By using the previously described modulation techniques, the wavelength separation is done electronically, and therefore it is not possible to determine by physical examination of the instrument which wavelengths out of the total set transmitted carry the information under test. Another benefit of this measurement technique is an extreme insensitivity to fixed frequency interfering signals, such as fluorescent lamps or other flashing lights. Since the signal is spread in frequency, and intersects with fixed frequency interferers over only a narrow part of its frequency range, the system is relatively insensitive to fixed frequency noise sources. Furthermore, such an algorithm provides high gain in the processed SNR by using a relatively wide bandwidth system and taking many measurement cycles per pixel.

Referring again to FIG. 3, the DSP 303 reorganizes and transforms the multi-spectral pixel data to produce monochromatic and transformed columns in top-to-bottom, left-to-right order. Transmitted intensities are converted by taking logarithms. The DSP 303 appends columns to 2D image buffers, and performs filtering and normalization, producing 8-bit filtered, normalized images for subsequent processing.

Example embodiments of the present invention may utilize algorithms implemented within the one or more DSPs 303 for the various recognition and authentication processes. Document images may be obtained, analyzed, and searched to detect and authenticate expected features of the document. The quality of match between detected and expected features, such as location, intensity, and reflectance spectrum, may be determined while compensating for various degrading effects such as soiling, wrinkling, translational, or rotational misalignment, etc., including banknotes that have material torn from or folded under each end. At each pixel location of all or a portion of a banknote, light intensity may be measured at a plurality of wavelengths to provide more than one image of a particular portion of the note.

The detection algorithms may process the data to determine certain features, such as denomination, series, facing, and/or orientation by the visible banknote image, denomination by IR transparent regions, if present, authentication of features with unique spectral properties if present, and/or multi-banknote events (1, 2, 3, or more overlaid notes). Verification of the previously listed requirements occurs regardless of the banknote series, flutter, tears, skew, and displacement.

Measurements taken over a large area of the note may be combined and averaged. This reduces the errors caused by faded ink and color variations, and improves the signal-to-noise ratio. An improved signal-to-noise ratio allows for better quality of measurement and better predictability and reproducibility. Displacement, skewing, and magnification may be compensated for by measuring the displacement and skew of each image and transforming and manipulating those images before subsequent processing. Flutter (displacement of the banknote in a direction generally not parallel with the direction of travel of the note) may cause apparent note shortening and may be compensated for by note magnification and scaling. Algorithms may be designed to allow for flutter by using a range of pixels in the corresponding images. Statistically, models used to measure features may compensate for a level of deviation between a predefined template and the real banknote. The algorithms may also recognize and accommodate either an unrestricted view of the surface of a banknote or a restricted view caused by machine transport belts or other transport apparatus, which may partially block a sensor housing's view of the surface of a banknote.

Raw pixel data may be interpreted and fed from the FPGA 301 into DSP 303, where spectral processing (i.e., processing of intensity versus wavelength) is performed. Note that partitioning of the algorithms between a plurality of DSPs 303 may be performed, (e.g., spatial information is processed (e.g., what inks are located where), and spectral information is processed (e.g., does the spectra of the inks match what is expected)), or partitioning between a plurality of DSPs 303 may be performed by note. For example, each new note may be assigned to the next free DSP 303. Furthermore, processing may be performed by a single DSP 303, as described in embodiments herein.

This multi-spectral data may be in single columns and re-organized and transformed into a set of monochromatic columns, each of which is derived from an individual wavelength or from arbitrary combinations of wavelengths. The reorganized, transformed image data is then used in spatial processing (i.e., processing of intensity vs. x, y spatial location). As columns of image data arrive, DSP 303 concatenates them into rectangular images and then begins subsequent processing when a predetermined number of columns have been received. The spatial algorithms are employed to determine denomination, facing, and orientation, to authenticate based on spectral features, and to sense multiple overlaid notes. For example, the DSP 303 may process the data and compare it against previously inputted templates of authentic and/or counterfeit banknotes, which may have been scanned with the system to thereby input their respective characteristics, which are then compared to a stream of actual banknotes to be examined. When this analysis has been completed, the results are exported where codes are generated for external reporting 304.

Normalizing may be performed using a known model based on expected intensity of the paper and dark ink (i.e., by monitoring its reflectance). Normalization may be performed to compensate for faded inks, soiled paper, operational differences between LEDs and/or detectors, and associated amplifiers, etc. Normalization may require comparison operations based on well-known data stored in memory as a baseline for the expected image characteristics. For example, model banknote data may include various denominations and other characteristics of the note that are predefined and stored in a database for data processing and comparison purposes. The raw data extracted may be processed and compared to the predefined note data.

The raw image data is analyzed to measure intensity distribution and spatial alignment, then translated, and scaled to normalize for subsequent processing. More specifically, in the multi-spectral image normalization, images at each wavelength may be normalized by adaptively equalizing black and white levels. The black and white levels for each wavelength may be adaptively estimated by an iterative method of intensity histogram estimation. Offsets and gains are calculated based on the measured black and white levels at each wavelength. Images are normalized using calculated offsets and gains. Certain characteristics may be determined by the algorithms performed by the DSP 303, such as denomination verification, feature recognition, orientation, faced or miss-faced, and/or thickness.

As previously noted, the banknotes are transported through the sensor device by a transport system of conveyance. The variability of the transport system can introduce measurement variability into the image acquisition, such as registration changes due to variable speed of motion. This variability may be compensated for by measuring and utilizing the speed of the transport in the time reference of the sensor to ensure proper image reconstruction.

Transports may also use belts or cables that potentially block the view of one side of each note. Median characteristic responses of the detectors are estimated and iteratively updated. Detectors obstructed by belts are identified by significant deviation from median characteristic responses. Pixels corresponding to obstructed detectors are eliminated from consideration in further algorithms. Alternatively, obstructed pixels may be replaced by interpolation of neighboring visible pixels, where such data provides a useful basis to make subsequent authentication decisions.

The denomination, series, facing, and orientation of each note may be identified by locating and classifying multiple image features on each side of the note. Notes may be accepted as authentic or rejected as counterfeit by a classical statistical pattern detection and classification method—essentially, a pattern recognition process in multidimensional space. First, multiple physical features are located and classified by general size, shape, and location. Next, pixels within the perimeter of each feature are weighted by their probability of being part of that feature, based on spatial correlation with expected feature shape, and spectral correlation with expected ink color and density. Then, the cumulative mean spectrum of each physical feature is estimated by combining the measured intensity of spatially and spectrally weighted pixels. Then, the spectrum vector may be augmented by appending additional metrics which are nonlinear functions of the spectrum. Such functions may be chosen from a large parametric family by determining optimal parameters to maximize separation among classes and between most similar class pairs. Next, the measured mean spectrum is classified by a maximum a-posteriori classifier, i.e., by combining probability density for each of multiple authentic and counterfeit spectral classes, prior expected class probabilities, and conditional rejection based on a minimum probability constraint. An IR transparent region denomination feature in the banknote may be detected, if present, and correlated with denomination as determined from visible image features.

Figure 17:
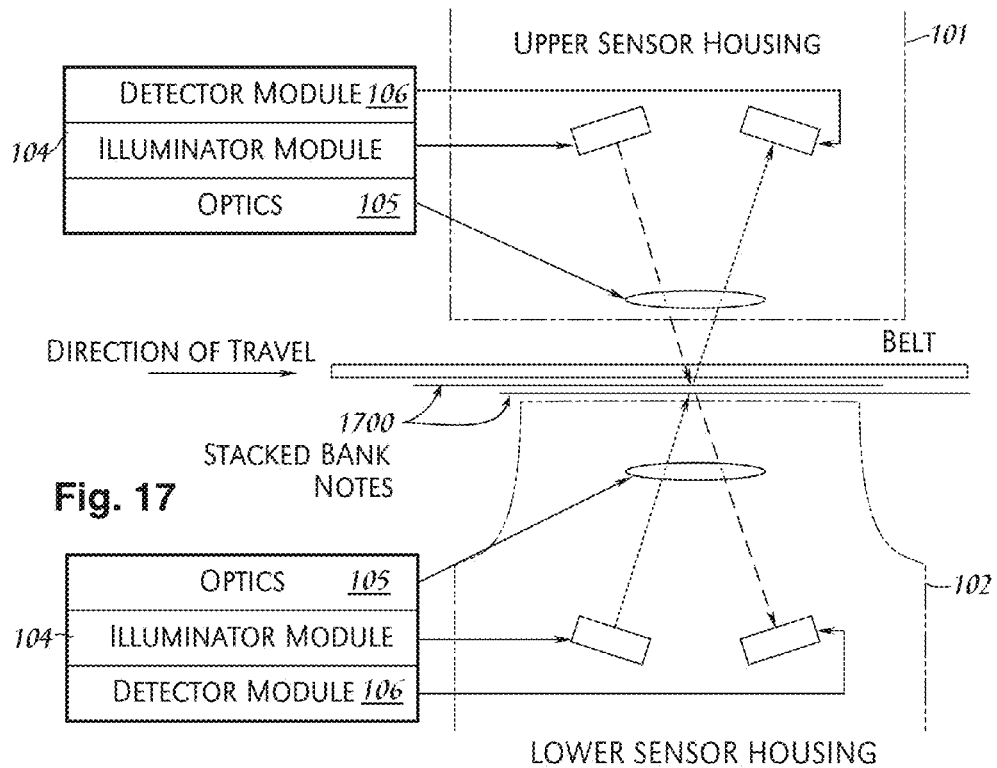
FIG. 17 illustrates an example sensor configuration, according to example embodiments of the present invention.

FIG. 17 illustrates a sensor device that detects multiple notes stacked 1700 at the same time, according to example embodiments of the present invention. Referring to FIG. 17, the sensor device may detect and count multiple stacked notes 1700 by measuring accumulated optical transmission loss. Light passing through single or multiple notes may be used to identify a presence of multiple stacked notes 1700. The scattered light from the upper housing module 101 passes through each note and is captured by the lower housing 102 optics and vice versa, thereby identifying multi-note events, without being affected by changes in minute paper densities, such as the security thread and watermark. Note, the dashed line represents light traveling from the upper sensor housing 101 to the lower sensor housing 102 and the dotted line represents light traveling from the lower sensor housing 102 to the upper sensor housing 101.

For example, stacked note detection may be achieved using a "transmission mode imaging" of the authentication optical system. In this mode of operation, approximately 10% of the light from the upper sensor housing 101 illuminator LED array 104 passes through the banknote and is scattered off the lower surface of the note. Similarly 10% of the light from the lower sensor housing 102 passes through the banknote and is scattered off the upper surface of the note. The upper and lower housing photodiode imaging arrays 106 and associated electronics measure the amount of light transmitted through the note and determines whether the banknote has the attenuation characteristics of a single note, two stacked notes, or more than two stacked notes. The transmission image collected by each sensor can also be a multi-spectral stack of two-dimensional images of the note.

Each pixel layer of the stack represents the intensity of a single wavelength of light remaining after it passes through the note. Alternatively, all wavelengths of the LED array may be turned on in any combination or simultaneously to create transmission signals of higher intensity but reduced spectral resolution. Sacrifice of spectral resolution for increased signal can be very advantageous in measurements of properties of limited spectral interest and low transmission, such as found in banknote thickness determinations over white or black areas.

The operations of a method or algorithm described in connection with the embodiments disclosed herein may be embodied directly in hardware, in a computer program executed by a processor, or in a combination of the two. A computer program may be embodied on a computer readable medium, such as a storage medium. For example, a computer program may reside in random access memory ("RAM"), flash memory, read-only memory ("ROM"), erasable programmable read-only memory ("EPROM"), electrically erasable programmable read-only memory ("EEPROM"), registers, hard disk, a removable disk, a compact disk read-only memory ("CD-ROM"), or any other form of storage medium known in the art.

Figure 19:
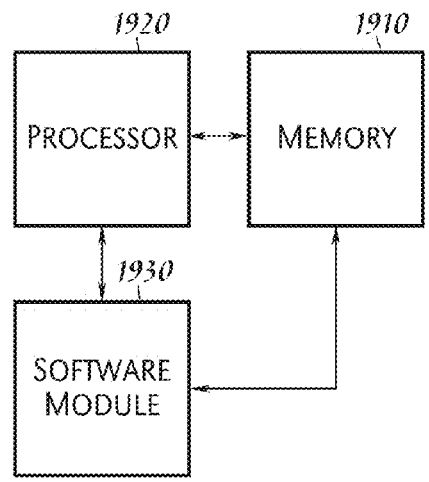
FIG. 19 illustrates an example computer entity configured to perform operations disclosed in various embodiments of the present invention.
Figure 20:
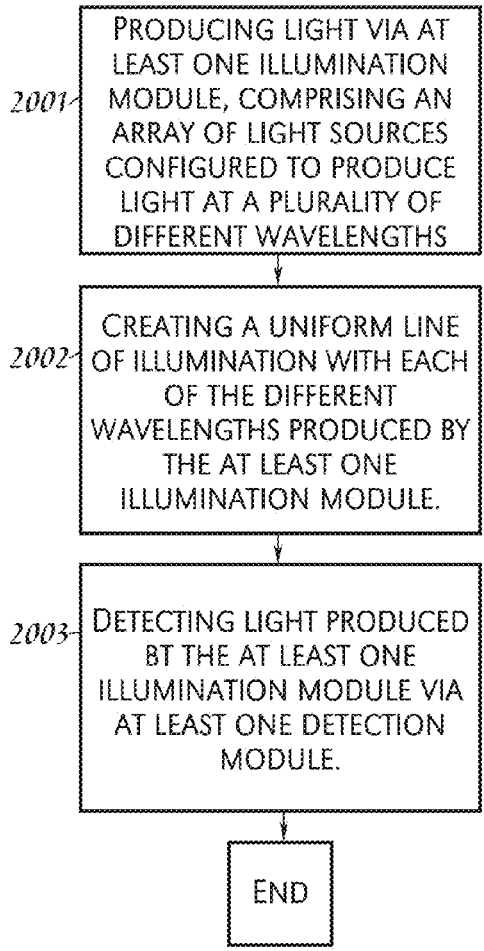
FIG. 20 illustrates a flow diagram of an example method, according to example embodiments of the present invention.

An exemplary storage medium may be coupled to the processor such that the processor may read information from, and write information to, the storage medium. In the alternative, the storage medium may be integral to the processor. The processor and the storage medium may reside in an application specific integrated circuit ("ASIC"). In the alternative, the processor and the storage medium may reside as discrete components. For example, FIG. 19 illustrates an example network element 1900, which may represent any of the above-described components of the previous drawings. A memory 1910 and a processor 1920 may be discrete components of the network entity 1900 that are used to execute an application or set of operations. The application may be coded in software in a computer language understood by the processor 1920, and stored in a computer readable medium, such as the memory 1910. The computer readable medium may be a non-transitory computer readable medium that includes tangible hardware components in addition to software stored in memory. Furthermore, a software module 1930 may be another discrete entity that is part of the network entity 1900, and which contains software instructions that may be executed by the processor 1920. In addition to the above noted components of the network entity 1900, the network entity 1900 may also have a transmitter and receiver pair configured to receive and transmit communication signals (not shown).

An example method of producing multi-spectral imaging of a plurality of line scan elements is disclosed. The method may include producing light via at least one illumination module at operation 2001, comprising an array of light sources configured to produce light at a plurality of different wavelengths. The method may also include creating a uniform line of illumination with each of the different wavelengths produced by the at least one illumination module, at operation 2002, and detecting light produced by the at least one illumination module via at least one detection module at operation 2003.

While embodiments of the present invention have been described, it is to be understood that the embodiments described are illustrative only, and the scope of the invention is to be defined solely by the appended claims when considered with a full range of equivalents and modifications (e.g., protocols, hardware devices, software platforms, etc.) thereto.

What is claimed is:

1. A method for authenticating an object, comprising:
   illuminating the object with a plurality of wavelengths of light from a plurality of light-emitting sources;
   detecting light scattered from the illuminated object with a plurality of photodiodes to create a multi-spectral image of at least a specified portion of the illuminated object, wherein the plurality of light-emitting sources and the plurality of photodiodes are optically coupled such that the plurality of wavelengths of light are simultaneously directed to the plurality of photodiodes;

producing a reflectance spectrum from the multi-spectral image, wherein the producing the reflectance spectrum from the multi-spectral image further comprises finding pixels of a specified feature on the object and averaging their intensity values;

comparing the reflectance spectrum to a template reflectance spectrum of an authentic object; and determining if the illuminated object is authentic as a function of the comparison.

2. The method as recited in claim 1, wherein the multi-spectral image of the illuminated object comprises a plurality of images of the illuminated object, wherein each of the plurality of images represents detected scattered light produced by one of the plurality of light-emitting sources.

3. The method as recited in claim 1, wherein the illuminating is performed as a line scan illumination of the object, wherein the line scan illumination is performed as the object moves past the plurality of light-emitting sources.

4. The method as recited in claim 3, wherein the plurality of light-emitting sources are configured into a two-dimensional array.

5. The method a recited in claim 4, wherein a first one of the light-emitting sources emits light in a first band of light wavelengths, and wherein a second one of the light-emitting sources emits light in a second band of light wavelengths, wherein the first and second bands are different from each other.

6. The method as recited in claim 1, wherein the plurality of photodiodes are arranged in a two-dimensional array.

7. The method as recited in claim 6, wherein a first one of the photodiodes comprises a silicon photodiode, and a second one of the photodiodes comprises an InGaAs photodiode.

8. The method as recited in claim 1, wherein the determining if the illuminated object is authentic further comprises determining that the object is a counterfeit when one or more intensity values in the reflectance spectrum is outside of a specified range of acceptable intensity values from the template reflectance spectrum.

9. The method as recited in claim 1, wherein each pixel on the specified portion of the object is simultaneously illuminated with more than one of the plurality of light-emitting sources.

10. The method as recited in claim 1, wherein the template reflectance spectrum of the authentic object is associated with a portion of the authentic object that spatially corresponds with the specified portion of the illuminated object.

11. The method as recited in claim 1, wherein the reflectance spectrum represents intensities of the detected scattered light from at least one spatial position of the illuminated object over the plurality of wavelengths of light resulting from the illumination from the plurality of light emitting sources.

12. The method as recited in claim 1, wherein the determining if the illuminated object is authentic further comprises determining that the object is authentic when a predetermined amount of the reflectance spectrum is within a specified range of the template reflectance spectrum.

13. The method as recited in claim 1, wherein the object is a banknote.

14. The method as recited in claim 1, wherein the plurality of light-emitting sources and the plurality of photodiodes are optically coupled via a multi-lens optical system.

15. The method as recited in claim 14, wherein the multi-lens optical system comprises a illuminator module comprising a plurality of lenses and a mirror.

16. The method as recited in claim 15, wherein the illuminator module collects and mixes the plurality of wavelengths of light from the plurality of light-emitting sources to form a relatively uniform line of light and directs the line of light upon the object.

17. The method as recited in claim 16, wherein the multi-lens optical system comprises a detector lens assembly comprising a plurality of lenses.

18. The method as recited in claim 17, wherein the detector lens assembly comprising a plurality of doublet lenses.

19. The method as recited in claim 18, wherein the detector lens assembly collects the light scattered from the illuminated object and directs the collected light onto the plurality of photodiodes.

20. The method of claim 19, wherein the detector lens assembly resolves a size of a feature on the object to match a size of the plurality of photodiodes.

21. A system for authenticating an object comprising:

a scanner configured for scanning at least a portion of the object and creating a reflectance spectrum thereof, wherein the reflectance spectrum is created from a multi-spectral image produced by the scanning of the at least the portion of the object, finding pixels of a specified feature on the object, and averaging their intensity values, wherein the multi-spectral image comprises a plurality of images each representing scattered light produced as a result of illumination by one of a plurality of light-emitting sources in the scanner and detected by a plurality of photodiodes in the scanner;

a multi-lens optical system in the scanner for coupling the plurality of light-emitting sources and the plurality of photodiodes such that such that the plurality of wavelengths of light are simultaneously directed to the plurality of photodiodes;

circuitry configured for comparing the reflectance spectrum to a template reflectance spectrum of an authentic object; and circuitry configured for determining whether the object is authentic as a function of the comparison.

* * * * *